United States Patent [19]

Bosies et al.

[11] Patent Number: 4,777,163
[45] Date of Patent: Oct. 11, 1988

[54] DIPHOSPHONATE DERIVATIVES, PHARMACEUTICAL COMPOSITIONS AND METHODS OF USE FOR CALCIUM DISTURBANCES

[75] Inventors: Elmar Bosies, Weinheim; Rudi Gall, Hirschberg, both of Fed. Rep. of Germany

[73] Assignee: Boehringer Mannheim GmbH, Mannheim, Fed. Rep. of Germany

[21] Appl. No.: 77,228

[22] Filed: Jul. 24, 1987

[30] Foreign Application Priority Data

Aug. 1, 1986 [DE]  Fed. Rep. of Germany ....... 3626058

[51] Int. Cl.$^4$ .................. A61K 31/675; C07F 9/65
[52] U.S. Cl. ......................... 514/80; 514/92; 514/93; 514/94; 514/96; 514/97; 514/98; 514/100; 514/101; 548/112; 548/113; 548/119; 549/7; 549/220; 549/221
[58] Field of Search ............ 548/112, 113, 119; 549/7, 220, 221; 514/80, 92, 93, 94, 96, 97, 98, 100, 101

[56] References Cited

U.S. PATENT DOCUMENTS 4,503,049 5/1985 Biere et al. .......................... 514/80
4,687,767 8/1987 Bosies et al. ....................... 514/89

FOREIGN PATENT DOCUMENTS 3203308 7/1983 Fed. Rep. of Germany.

OTHER PUBLICATIONS

Benedict et al, Chemical Abstracts, vol. 105 (1986) 232453q.

Primary Examiner—Richard L. Raymond
Attorney, Agent, or Firm—Felfe & Lynch

[57] ABSTRACT

The present invention produces alkyldiphosphonic acid derivative of the general formula:

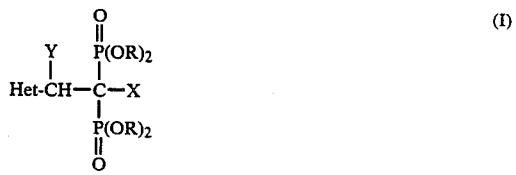

wherein Het is a heteroaromatic five-membered ring containing to 3 heteroatoms which can be partly hydrogenated and optionally substituted one or more times by alkyl, alkoxy, phenyl, cyclohexyl, cyclohexylmethyl, halogen or amino, and two adjacent alkyl substituents can together also form a ring, Y is a hydrogen atom or a lower alkyl radical, X is a hydrogen atom, a hydroxyl group or an amino group optionally substituted by lower alkyl and R is a hydrogen atom or a lower alkyl radical, with the proviso that Het is not a pyrazole ring; as well as the pharmacologically acceptable salts thereof.

The present invention also provides processes for the prepearation of these compounds and pharmaceutical compositions containing them useful for the treatment or prophylaxis of calcium metabolism disturbances or disease as for example osteoporosis, Bechterew's disease, bone metastases, urolithiasis, heterotropic ossifications, rheumatoid arthritis osteoarthritis or degenerative arthrosis.

21 Claims, No Drawings

DIPHOSPHONATE DERIVATIVES, PHARMACEUTICAL COMPOSITIONS AND METHODS OF USE FOR CALCIUM DISTURBANCES

The present invention is concerned with new diphosphonic acid derivatives, processes for the preparation thereof and pharmaceutical compositions containing them.

In DE-OS Nos. 32 03 307 and 32 03 308 there are described arylethanediphosphonates, for example thienylethanediphosphonate and a pyrazolethanediphosphonate with outstanding anti-inflammatory action.

In Federal Republic of Germany Patent Specification No. 18 13 659, there are described diphosphonic acid derivatives of which 1-hydroxyethane-1,1-diphosphonic acid has achieved importance as an agent for the treatment of Paget's disease. In European Patent Specification No. 0,186,405, there are described, inter alia, pyridylalkyldiphosphonates and in Federal Republic of Germany Patent Specification No. 34 28 524 there are described heteroaromatic alkyldiphosphonates in which the alkylene chain contains at least 2 carbon atoms.

We have now found that analogous derivatives of these compounds in which there is only one carbon atom between the diphosphonate residue and the heterocyclic radical and the heterocycle is not a pyrazole ring also display these actions and, in addition, as good calcium complex formers, are suitable for the wider treatment of calcium metabolism disturbances. In particular, they can be very well used in cases in which the bone formation and breakdown is disturbed, i.e. they are suitable for the treatment of diseases of the skeletal system, for example osteoporosis, Bechterew's disease and the like.

However, on the basis of these properties, they can also be used in the therapy of bone metastases or or urolithiasis and for the prevention of heterotopic ossifications. Furthermore, due to their influencing of the calcium metabolism, they form a basis for the treatment of rheumatoid arthritis, osteoarthritis and degenerative arthrosis.

Consequently, according to the present invention, there are provided diphosphonates of the general formula:

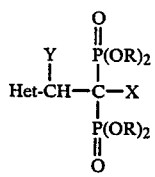
(I)

wherein Het is a heteroaromatic five-membered ring containing 2 or 3 heteroatoms which can be partly hydrogenated and optionally substituted one or more times by alkyl, alkoxy, phenyl, cyclohexyl, cyclohexylmethyl, halogen or amino, whereby two adjacent alkyl substituents can together also form a ring, Y is a hydrogen atom or a lower alkyl radical, X is a hydrogen atom, a hydroxyl group or an amino group optionally substituted by lower alkyl and R is a hydrogen atom or a lower alkyl radical, with the proviso that Het cannot be a pyrazole ring; as well as the pharmacologically acceptable salts thereof.

Of the 2 or 3 heteroatoms in the heteroaromatic five-membered ring, as a rule, one heteroatom is a nitrogen atom. Preferred heteroaromatic rings include the imidazole, imidazoline, isoxazole, oxazole, oxazoline, thiazole, thiazoline, triazole, oxadiazole and thiadiazole radicals.

Alkyl means itself or in an alkoxy radical, a hydrocarbon radical containing up to 4 carbon atoms and preferably a methyl, ethyl or isobutyl radical. Two adjacent alkyl substituents on the heteroaromatic five-membered ring can together also form a ring and preferably a six-membered ring.

By halogen are to be understood fluorine, chlorine, bromine and iodine, chlorine being preferred.

Compounds in which two alkyl radicals together form a ring can be present as stereoisomeric mixtures or as pure cis-or trans-isomers.

Asymmetric carbon atoms can have the R-, S- or R,S-configuration.

Compounds of general formula (I) are prepared according to known processes.

When X in general formula (I) is a hydroxyl group, the new compounds are preferably prepared in that (a) a carboxylic acid of the general formula:

(II)

in which Het and Y have the above-given meanings, is reacted with a mixture of phosphorous acid or phosphoric acid and a phosphorus halide and subsequently saponified to the free diphosphonic acid, or (b) a carboxylic acid chloride of the general formula:

(III)

in which Het and Y have the above-given meanings, is reacted with a trialkyl phosphite of the general formula:

(IV), in which R' is a lower alkyl radical, to give an acyl phosphonate of the general formula:

(V)

in which Het, Y and R' have the above-given meanings, which is subsequently reacted with a dialkyl phosphite of the general formula:

(VI)

in which R' has the above-given meaning, to give a diphosphonate of the general formula:

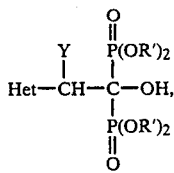

(VII)

in which Het, Y and R' have the above-given meanings, and the tetraester obtained is optionally saponified to the corresponding diester or acid of general formula (I);

or when X in general formula (I) is an amino group optionally substituted by alkyl radicals, (c) a carboxylic acid derivative of the general formula:

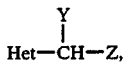

(VIII)

in which Het and Y have the above-given meanings and Z is a nitrile, iminoether or N,N-dialkylcarboxamido radical, is reacted with a phosphorus compound of the general formula:

(IX), in which T is a halogen atom, a hydroxyl group of OR', R' having the above-given meaning, and subsequently optionally saponified;

or when X in general formula (I) is a hydrogen atom, (d) a compound of the general formula:

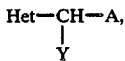

(X)

in which Het and Y have the above-given meanings and A is a reactive residue, for example a halogen atom or a sulphonate group, is reacted with a compound of the general formula:

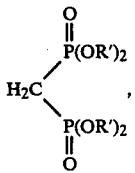

(XI)

in which R' has the above-given meaning, to give a diphosphonate of the general formula:

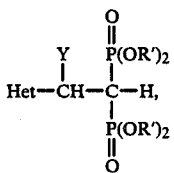

(XII)

in which Het, Y and R' have the above-given meanings, and the tetra ester obtained is optionally saponified to the corresponding diester or acid of general formula (I).

The carboxylic acids of general formula (II) used in process (a) are reacted with 1 to 2 and preferably 1.5 mole of phosphorous acid or phosphoric acid and 1 to 2 and preferably 1.5 mole phosphorus trihalide at a temperature of from 80° to 130° C. and preferably of from 100° to 110° C. The reaction can also be carried out in the presence of diluents, for example halogenated hydrocarbons, especially chlorobenzene or tetrachloroethane, or also dioxan. The subsequent hydrolysis takes place by boiling with water but preferably with semi-concentrated hydrochloric or hydrobromic acid.

In the case of process (b), the acid chloride of general formula (III) is reacted with the trialkyl phosphite of general formula (IV) at a temperature of from 0° to 60° C. and preferably of from 20° to 40° C. It is possible to work without a solvent or also in the presence of an inert solvent, for example diethyl ether, tetrahydrofuran, dioxan or also a halogenated hydrocarbon, for example methylene chloride. The acyl phosphonate of general formula (V) formed as an intermediate can be isolated or further worked up directly.

The subsequent reaction is carried out in the presence of a weak base and preferably of a secondary amine, for example dibutylamine, at a temperature of from 0° to 60° C. and preferably of from 10° to 30° C.

In the case of process (c), the nitrile of general formula (VIII) is reacted with phosphorous acid at a temperature of from 110° to 180° C. The reaction can be carried out without or in the presence of an aprotic solvent, for example diglycol dimethyl ether or diglycol diethyl ether. However, the nitrile can also be reacted with a phosphorus trihalide, for example phosphorus trichloride or phosphorus tribromide, in an inert solvent, for example dioxan or tetrahydrofuran, optionally with the addition of water, at a temperature of from 20° to 80° C. Imino ethers of general formula (VIII) can be reacted with dialkyl phosphites preferably in the presence of an equimolar amount of sodium in an inert solvent, for example diethyl ether, dioxan or also benzene, the reaction usually taking place at the reflux temperature of the solvent employed. Acid amides of general formula (VIII) can be reacted in an inert solvent, for example a halogenated hydrocarbon or ether, for example diethyl ether, with a mixture of phosphorus pentahalide/phosphorous acid or also of oxalyl chloride/trialkyl phosphite.

In the case of process (d) the methylenediphosphonic acid ester of general formula (XI) is used in the form of its sodium or potassium salt. For this purpose, it is reacted with sodium or potassium or the corresponding hydride in an inert solvent, for example benzene, toluene, or dimethylformamide, at a temperature of from 0° to 40° C. and preferably of 25° C. The alkali metal salt is reacted, without isolation, with the appropriate halide or sulphonate, the temperature hereby being from 20° to 110° C.

The tetraalkyl esters possibly obtained in the case of processes (b), (c) and (d) can be saponified to diesters or to free tetra acids. the saponification to diesters takes place, as a rule, by treating the tetralkyl esters with an alkali metal halide, preferably sodium iodide, in an appropriate solvent, for example acetone, at ambient temperature. There is hereby formed the symmetrical diester/disodium salt which, if desired, can be converted by means of an acidic ion exchanger into the diester/diacid. The saponification to free diphosphonic acids takes place, as a rule, by boiling with hydrochloric or hydrobromic acid. However, a cleavage can also be carried out with a trimethylsilyl halide, preferably the bromide or iodide. On the other hand, the free diphosphonic acid can again be converted into a tetraalkyl ester by boiling with an orthoformic acid alkyl ester. The free diphosphonic acids of general formula (I) can be isolated as free acids or in the form of their mono- or dialkali metal or ammonium salts. As a rule, the alkali metal salts can be readily purified by reprecipitation from water/methanol or water/acetone.

If desired, the compounds of general formula (I) can subsequently be converted from one into another. They can, for example, be alkylated or, when X in general formula (I) signifies at unsubstituted amino group, can be converted by diazotisation into compounds of general formula (I) in which X is a hydroxyl group. By hydrogenolytic splitting off of an N-benzyl radical, there can be prepared, for example, the corresponding unsubstituted compounds of general formula (I).

As pharmacologically acceptable salts, there are used, in particular, alkali metal or ammonium salts which are prepared in the usual way, for example by neutralisation of the compounds with inorganic or organic bases, for example sodium or potassium carbonate, aqueous sodium or potassium hydroxide solutions, aqueous ammonia or amines, for example trimethylamine or triethylamine.

The new compounds of general formula (I) according to the present invention and the salts thereof can be administered enterally or parenterally in liquid or solid form. For this purpose, there can be used the conventional forms of administration, for example tablets, capsules, dragees, syrups, solutions, suspensions and the like. As injection medium, it is preferred to use water which contains the additives usual in the case of injection solutions, such as stabilising agents, solubilising agents and buffers.

Additives of this kind include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Liquid carrier materials for injection solutions must be sterile and are preferably placed into ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage can depend upon various factors, such as mode of administration, species, age and/or individual state. The dosages to be administered daily are from about 1 to 1000 mg. for humans and preferably from 10 to 200 mg. and can be taken once per day or divided up into several dosages.

Preferred in the sense of the present invention are, apart from the compounds described in the following Examples and the compounds derivable by combination of all of the meanings given in the claims, also the following diphosphonic acids, as well as the sodium salts and methyl and ethyl esters thereof:

1-hydroxy-2-(3-methyl-1,2,4-thiadiazol-5-yl)-ethane-1,1-diphosphonic acid
1-hydroxy-2-(3-phenyl-1,2,4-thiadiazol-5-yl)-ethane-1,1-diphosphonic acid
1-hydroxy-2-(3-cyclohexylmethyl-1,2,4-thiadiazol-5-yl)-ethane-1,1-phosphonic acid
1-hydroxy-2-(3-methylisoxazol-5-yl)-ethane-1,1-diphosphonic acid
1-hydroxy-2-(3-phenylisoxazol-5-yl)-ethane-1,1-diphosphonic acid
1-hydroxy-2-(3-methyl-1,2,5-oxadiazol-4-yl)-ethane-1,1-diphosphonic acid
1-hydroxy-2-(2-methyl-1,3,4-oxadiazol-5-yl)-ethane-1,1-diphosphonic acid
1-hydroxy-2-(3-phenyl-1,2,4-oxadiazol-5-yl)-ethane-1,1-diphosphonic acid
1-hydroxy-2-(1,2,3-thiadiazol-4-yl)-ethane-1,1-diphosphonic acid
1-hydroxy-2-(1,2,5-thiadiazol-4-yl)-ethane-1,1-diphosphonic acid
1-hydroxy-2-(4-oxazoline-2-yl)-ethane-1,1-diphosphonic acid
1-hydroxy-2-(5-methoxyoxazol-4-yl)-ethane-1,1-diphosphonic acid
1-hydroxy-2-(5-ethoxyoxazol-4-yl)-ethane-1,1-diphosphonic acid
1-hydroxy-2-(2-aminooxazol-4-yl)-ethane-1,1-diphosphonic acid
1-hydroxy-2-(2,5-dimethyloxazol-4-yl)-ethane-1,1-diphosphonic acid
1-hydroxy-2-(5-ethoxy-2-methyloxazol-4-yl)-ethane-1,1-diphosphonic acid
1-hydroxy-2-(2-methyl-1,3,4-oxadiazol-5-yl)-ethane-1,1-diphosphonic acid
1-hydroxy-2-(3-phenyl-1,2,4-oxadiazol-5-yl)-ethane-1,1-diphosphonic acid
1-hydroxy-2-(1,2,3-thiadiazol-5-yl)-ethane-1,1-diphosphonic acid
1-hydroxy-2-(4-methyl-1,2,3-thiadiazol-5-yl)-ethane-1,1-diphosphonic acid
1-hydroxy-2-(5-methylimidazol-4-yl)-ethane-1,1-diphosphonic acid
2-(2-methylthiazol-4-yl)-ethane-1,1-diphosphonic acid
2-(2-methylthiazol-4-yl)-propane-1,1-diphosphonic acid
1-hydroxy-2-(2-methylthiazol-5-yl)-ethane-1,1-diphosphonic acid
2-(2-methylthiazol-5-yl)-propane-1,1-diphosphonic acid
1-hydroxy-2-(1,2,3-triazol-4-yl)-ethane-1,1-diphosphonic acid
1-hydroxy-2-(1,2,4-triazol-3-yl)-ethane-1,1-diphosphonic acid
1-hydroxy-2-(2-aminoimidazol-4-yl)-ethane-1,1-diphosphonic acid
2-(2-methylthiazol-5-yl)-ethane-1,1-diphosphonic acid
1-hydroxy-2-(imidazol-4-yl)-propane-1,1-diphosphonic acid
1-hydroxy-2-(3a,4,5,6,7,7a-hexahydrobenzoxazol-2-yl)-ethane-1,1-diphosphonic acid
1-hydroxy-2-(3a,4,5,6,7,7a-hexahydrobenzthiazol-2-yl)-ethane-1,1-diphosphonic acid
2-(imidazol-4-yl)-ethane-1,1-diphosphonic acid
1-amino-2-(imidazol-4-yl)-ethane-1,1-diphosphonic acid
1-dimethylamino-2-(imidazol-4-yl)-ethane-1,1-diphosphonic acid
1-hydroxy-2-(2-cyclohexylmethyl-1,3,4-oxadiazol-5-yl)-ethane-1,1-diphosphonic acid
1-hydroxy-2-(2-cyclohexyl-1,3,4-oxadiazol-5-yl)-ethane-1,1-diphosphonic acid
1-hydroxy-2-(2-aminothiazol-5-yl)-ethane-1,1-diphosphonic acid
1-hydroxy-2-(2-chlorothiazol-5-yl)-ethane-1,1-diphosphonic acid
1-hydroxy-2-(2-chlorooxazol-4-yl)-ethane-1,1-diphosphonic acid
1-hydroxy-2-(imidazol-2-yl)-ethane-1,1-diphosphonic acid 1-hydroxy-2-(1,2,4-triazol-1-yl)-ethane-1,1-diphosphonic acid.

The following Examples show some of the process variants which can be used for synthesising the compounds according to the present invention. As a rule, the compounds are obtained in the form of high melting point (m.p.≧300° C.) solid products (mono- or disodium salts), the structures of which have been verified by H-, P- and possibly by 13C- NMR spectroscopy. The purity of the compounds was determined by means of C, H, N, P, S and Na analyses, as well as by thin layer electrophoresis (cellulose, oxalate buffer of pH 4.0). For the characterisation of the individual compounds, there are given the $M_{rel}$ values (relative mobilities) referred to pyrophosphate ($M_{rel}=1$).

EXAMPLE 1

1-Hydroxy-2-(imidazol-4-yl)-ethane-1,1-diphosphonic acid 3 g. Phosphorous acid are added to 3.5 g. imidazol-4-ylacetic acid hydrochloride (m.p. 198-200° C.) in 40 ml. chlorobenzene. The reaction mixture is stirred for 10 minutes at 110° C., cooled and 9 g. phosphorus trichloride slowly added dropwise thereto. The reaction mixture is heated for 16 hours to 110° C., cooled, the chlorobenzene is decanted off from an orange-coloured syrup and the residue is mixed with 50 ml. 6N hydrochloric acid. The suspension is heated under reflux for 5 hours, cooled, mixed with charcoal and filtered off with suction. The filtrate is evaporated, dried and boiled up with acetone for 2 hours. The residue (4.3 g.) is dissolved in water, the solution is adjusted with 2N aqueous sodium hydroxide solution to a pH of 5, mixed with methanol and the precipitate obtained is filtered off with suction. There are obtained 1.2 g. (about 16.9% of theory) of the desired product; m.p.>290° C. The compound is obtained as the monosodium salt containing 2 moles of water of crystallisation ($M_{rel}=0.37$).

EXAMPLE 2

In a manner analogous to that described in Example 1, there are obtained, by the reaction of phosphorous acid and phosphorus trichloride with (a) 2-methylthiazol-4-ylacetic acid (m.p. 119°-121° C., prepared by saponification of the corresponding ethyl ester (b.p. 127° C./13 mm.Hg; which is prepared according to J. Chem. Soc., 1946, 91 from ethyl γ-bromoacetoacetate by reaction with thioacetamide), 1-hydroxy-2-(2-methylthiazol-4-yl)-ethane-1,1-diphosphonic acid which is isolated as the disodium salt containing 1 mole of water of crystallisation in a yield of 57% of theory; m.p.>300° C.; $M_{rel}=0.55$.

(b) 3a,4,5,6,7,7a-hexahydrobenzimidazol-2-ylacetic acid (m.p. 168°-170° C.; prepared by saponification of the ethyl ester (m.p. 141°-143° C.; which is prepared by reacting 1,2-diaminocyclohexane with the imino ether of ethyl cyanoacetate), 1-hydroxy-2-(3a,4,5,6,7,7a-hexahydrobenzimidazol-2-yl)-ethane-1,1-diphosphonic acid which is isolated as the sodium salt containing 2 mole of water of crystallisation in a yield of 12% of theory; m.p.>300° C.; $M_{rel}=0.45$.

(c) 4-imidazolin-2-ylacetic acid (m.p. 108°-110° C.; prepared by saponification of the ethyl ester (m.p. 102°-105° C.), which is prepared by reacting ethylenediamine with the imino ether of ethyl cyanoacetate), 1-hydroxy-2-(4-imidazolin-2-yl)-ethane-1,1-diphosphonic acid which is isolated as the free acid with 1 mole of water of crystallisation in a yield of 14% of theory; m.p. about 250° C. (decomp.); $M_{rel}=0.45$.

(d) 2-amino-4-thiazolin-4-ylacetic acid (m.p. 218°-221° C.; prepared by saponification of the ethyl ester (oily substance) which is prepared by reacting thiourea with ethyl γ-bromoacetoacetate), 2-(2-amino-4-thiazolin-4-yl)-ethane-1-hydroxy-1,1-diphosphonic acid which is isolated as the free acid with 2 moles of water of crystallisation in a yield of 59% of theory; m.p. 190°-195° C. (decomp.); $M_{rel}=0.40$.

EXAMPLE 3

Tetraethyl-2-(1,2,5-thiadiazol-4-yl)-ethane-1,1-diphosphonate

A solution of 1.62 g. tetraethyl methanediphosphonate in 10 ml. anhydrous toluene is added dropwise to 0.2 g. sodium hydride (69%) in 10 ml. anhydrous toluene. After termination of the evolution of hydrogen, 1 g. 4-bromomethyl-1,2,5-thiadiazole in 10 ml. anhydrous toluene is added thereto and the reaction mixture stirred for 12 hours at ambient temperature. A little water is then added and the organic phase is separated off, dried and evaporated. The residue is purified over a column of silica gel (100 g.; elution agent methylene chloride/methanol 98:2 v/v). There is thus obtained 1.18 g. of the desired product in the form of a colourless oil; yield 55% of theory.

EXAMPLE 4

2-(1,2,5-Thiadiazol-4-yl)-ethane-1,1-diphosphonic acid 1.18 g. of the tetraethyl 2-(1,2,5-thiadiazol-4-yl)-ethane-1,1-diphosphonate described in Example 3 is mixed with 3.3 ml. trimethylbromosilane under an atmosphere of nitrogen. The reaction mixture is left to stand for 24 hours at ambient temperature and the solution is then evaporated, the residue is mixed with water, the solution is adjusted to a pH of 5 with sodium hydroxide and mixed with methanol. The precipitate obtained is filtered off with suction. There is thus obtained 0.56 g. (53% of theory)of the desired diphosphonic acid in the form of the disodium salt with 1 mole of water of crystallisation; m.p.>300° C.; $M_{rel}=0.9$.

TEST REPORT Male Wistar rats from our own breeding weighing about 160 g were thyroparathyroidectomized on day 1. On day 5, the success of the operation was controlled by measuring calcemia after a night fasting. From that day on, all the animals were group-fed, that means all of them ate the same quantity of food. Furthermore, the animals received then daily for 3 days 2 subcutaneous injections, on containing 25 μug of a synthetic retinoid, the other one the bisphosphonate to be tested, Additionally, all animals were given 2 μug of thyroxine the first and last day of treatment. 24 h after the last injection of the retinoid and the bisphosphonate and after one night fasting, blood was taken by retroorbital puncture under ether anesthesia. Plasma calcium was then analyzed by means of atomic absorption. The table shows the various doses compared with 1-hydroxyethane1.1-diphosphonate acid.

TABLE

| Example No. | mg P/kg | | | | |
| --- | --- | --- | --- | --- | --- |
| | 0.001 | 0.01 | 0.1 | 1 | 10 |
| 2c | | + | +++ | | |
| 1 | (+) | +++ | +++ | +++ | +++ |
| 1-hydroxy-ethane- | 0 | 0 | 0 | 0 | (+) |

TABLE-continued

| | mg P/kg | | | | |
|---|---|---|---|---|---|
| Example No. | 0.001 | 0.01 | 0.1 | 1 | 10 |
| 1.1-diphosphonic acid (from DE-OS 18 13 659) | | | | . | 5 |

0 = Depression of Hypercalcaemie - 0,99 bis + 0,99 mg %
(+) = Depression of Hypercalcaemie - 1,0 bis + 1,99 mg %
+ = Depression of Hypercalcaemie - 2,0 bis + 2,99 mg %
++ = Depression of Hypercalcaemie - 3,0 bis + 3,99 mg %
+++ = Depression of Hypercalcaemie - >4,0 %

It will be understood that the specification and examples are illustrative but not limitative of the present invention and that other embodiments within the spirit and scope of the invention will suggest themselves to those skilled in the art.

We claim:

1. An alkyldiphosphonic acid derivative of the formula:

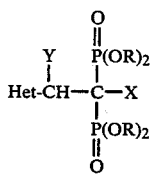

wherein

Het is a substituted or unsubstituted heteroaromatic five-membered first ring selected from the group consisting of imidazolyl, imidazolinyl, isoxazolyl, oxazolyl, oxazolinyl, thiazolyl, thiazolinyl, triazolyl, oxadiazolyl and thiadiazolyl wherein said ring can be partly hydrogenated and wherein said substituents are selected from at least one of the group consisting of $C_1$-$C_4$ alkyl, $C_1$-$C_4$ alkoxy, phenyl, cyclohexyl, cyclohexylmethyl, halogen and amino, and wherein two adjacent alkyl substitutents of Het can together form a second ring, Y is hydrogen or a $C_1$-$C_4$ alkyl, X is hydrogen, hydroxyl, amino, or an amino group substituted by $C_1$-$C_4$ alkyl, and R is hydrogen or a $C_1$-$C_4$ alkyl, as well as the pharmacologically acceptable salts and isomers thereof.

2. A compound of claim 1 wherein two adjacent alkyl substituents of Het together form a second ring, which bicyclic ring is hexahydrobenzimidazolyl, hexahydrobenzoxazolyl or hexahydrobenzthiazolyl.

3. The compound of claim 1 wherein the substituents are methyl, ethyl, isobutyl, methoxyethoxy, halogen or amino.

4. The compound of claim 1 wherein the second ring is a six-membered ring.

5. The compound of claim 1 wherein the halogen is fluorine, chlorine, bromine or iodine.

6. The compound of claim 1 wherein the halogen is chlorine.

7. The compound of claim 1 wherein Y is H or methyl.

8. The compound of claim 1 wherein X is hydrogen, hydroxy, amino or dimethylamino.

9. The compound of claim 1 wherein X is hydrogen or hydroxy.

10. The compound of claim 1 wherein R is hydrogen, methyl or ethyl.

11. The compound of claim 1 designated 1-hydroxy-2-(imidazole-4-yl)-ethane-1,1-diphosphonic acid and the physiologically active salt.

12. The compound of claim 1 designated 1-hydroxy-2-(4-imidazoline-2-yl)-ethane-1,1-diphosphonic acid and the physiologically active salt.

13. The compound of claim 1 designated 2-(2-amino-4-thiazoline-4-yl)-ethane-1-hydroxy-1,1-diphosphonic acid and the physiologically active salt.

14. A pharmaceutical composition for the treatment or prophylaxis of calcium metabolism disturbance or disease containing an effective amount of at least one compound of claim 1 in a pharmaceutically acceptable carrier.

15. A pharmaceutical composition for the treatment or prophylaxis of calcium metabolism disturbance or disease containing an effective amount of at least one compound of claim 3 in a pharmaceutically acceptable carrier.

16. A pharmaceutical composition for the treatment or prophylaxis of calcium matabolism disturbance or disease containing an effective amount of at least one compound from the group of 1-hydroxy-2-(imidazole-4-yl)-ethane-1,1-diphosphonic acid, 1-hydroxy-2-(4-imidazoline-2-yl)-ethane-1,1-diphosphonic acid and 2-(2-amino-4-thiazoline-4-yl)-ethane-1-hydroxy-1,1-diphosphonic acid in a pharmaceutilatty acceptable carrier.

17. A method for the treatment or prophylaxis of calcium metabolism disturbance or disease comprising administering an effective amount of at least one of a pharmaceutically acceptable compound of claim 1.

18. A method for the treatment or prophylaxis of calcium metabolism disturbance or disease comprising administering an effective amount of at least one of a pharmaceutically acceptable compound of claim 4.

19. A method for the treatment of prophylaxis of calcium metabolism disturbance or disease comprising administering an effective amount of at least one pharmaceutically acceptable compound selected from the group consisting of 1-hydroxy-2-(imidazole-4-yl)-ethane-1,1-diphosphonic acid, 1-hydroxy-2-(4-imidazoline-2-yl)-ethane-1,1-diphosphonic acid and 2-(2-amino-4-thiazoline-4-yl)-ethane-1-hydroxy-1,1-diphosphonic acid.

20. The method of claim 17 wherein the dose is 0.001–10 mg P/kg.

21. The method of claim 18 or 19 wherein the dose is 0.001–10 mg P/kg.

* * * * *